United States Patent
Albers

(10) Patent No.: US 11,743,642 B2
(45) Date of Patent: Aug. 29, 2023

(54) MICROPHONE ASSEMBLY WITH FREE FALL DETECTION

(71) Applicant: Knowles Electronics, LLC, Itasca, IL (US)

(72) Inventor: John Albers, Chicago, IL (US)

(73) Assignee: KNOWLES ELECTRONICS, LLC., Itasca, IL (US)

( * ) Notice: Subject to any disclaimer, the term of this patent is extended or adjusted under 35 U.S.C. 154(b) by 119 days.

(21) Appl. No.: 17/602,916

(22) PCT Filed: Apr. 3, 2020

(86) PCT No.: PCT/US2020/026532
§ 371 (c)(1),
(2) Date: Oct. 11, 2021

(87) PCT Pub. No.: WO2020/210120
PCT Pub. Date: Oct. 15, 2020

(65) Prior Publication Data
US 2022/0182759 A1 Jun. 9, 2022

Related U.S. Application Data

(60) Provisional application No. 62/832,944, filed on Apr. 12, 2019.

(51) Int. Cl.
*H04R 3/00* (2006.01)
*H04R 29/00* (2006.01)
(Continued)

(52) U.S. Cl.
CPC ............... *H04R 3/007* (2013.01); *H04R 1/08* (2013.01)

(58) Field of Classification Search
CPC . H04R 1/00; H04R 1/08; H04R 1/028; H04R 1/04; H04R 1/10; H04R 1/1041;
(Continued)

(56) References Cited

U.S. PATENT DOCUMENTS 9,706,294 B2 7/2017 Kopetz et al.
2008/0049953 A1* 2/2008 Harney ................... H04R 1/245
381/94.7
(Continued)

FOREIGN PATENT DOCUMENTS

CN 108307065 A * 7/2018 ........ H04M 1/72454
CN 108347528 A * 7/2018 ............ H04M 1/026
(Continued)

OTHER PUBLICATIONS

International Preliminary Report on Patentability on Appl. Ser. No. PCT/US2020/026532 dated Oct. 21, 2021 (9 pages).
(Continued)

*Primary Examiner* — Thang V Tran
(74) *Attorney, Agent, or Firm* — Foley & Lardner LLP

(57) ABSTRACT

A microphone assembly includes an acoustic transducer configured to generate an analog signal in response to pressure changes sensed by the acoustic transducer. The analog signal includes frequency components below a threshold frequency. The microphone assembly also includes an integrated circuit electrically coupled to the acoustic transducer and configured to determine a characteristic of frequency components below the threshold frequency, determine whether the characteristic of the frequency components corresponds to a fall event, and generate an output signal in response to a determination that the characteristic of the frequency components corresponds to the fall event. The microphone assembly also includes a housing having an external device interface with electrical contacts. The acoustic transducer and the integrated circuit are disposed within the housing. The integrated circuit is electrically coupled to contacts of the external device interface.

20 Claims, 10 Drawing Sheets

(51) Int. Cl.
 *H04R 1/00* (2006.01)
 *H04R 1/08* (2006.01)
(58) Field of Classification Search
 CPC .......... H04R 3/00; H04R 3/002; H04R 3/007; H04R 25/30; H04R 25/305; H04R 25/603; H04R 2225/55
 See application file for complete search history.

(56) References Cited

U.S. PATENT DOCUMENTS

| | | | | |
|---|---|---|---|---|
| 2012/0324980 | A1* | 12/2012 | Nguyen | G11B 19/042 73/514.16 |
| 2013/0054180 | A1* | 2/2013 | Barfield | G01P 15/0891 702/141 |
| 2013/0257582 | A1* | 10/2013 | Rothkopf | H04M 1/185 340/3.1 |
| 2018/0054502 | A1* | 2/2018 | Wilson | B65D 81/02 |
| 2020/0007995 | A1* | 1/2020 | Pedersen | H04R 25/356 |

FOREIGN PATENT DOCUMENTS

| | | | | | |
|---|---|---|---|---|---|
| CN | 108377293 | A | * | 8/2018 | ........ H04M 1/72522 |
| CN | 108390999 | A | * | 8/2018 | ........ H04M 1/72569 |
| CN | 108769350 | A | * | 11/2018 | .............. H04M 1/24 |
| JP | 2004128547 | A | * | 4/2004 | .............. H04M 1/00 |
| WO | WO-2016/083294 | A1 | | 6/2016 | |
| WO | WO-2018/129242 | A1 | | 7/2018 | |

OTHER PUBLICATIONS

International Search Report and Written Opinion on Appl. Ser. No. PCT/US2020/026532 dated Jul. 24, 2020 (14 pages).

* cited by examiner

MICROPHONE ASSEMBLY WITH FREE FALL DETECTION

CROSS-REFERENCE TO RELATED APPLICATIONS

This application is the U.S. National Stage entry of P.C.T Application No. PCT/US2020/026532 filed Apr. 3, 2020, which claims the benefit of and priority to U.S. Provisional Patent Application No. 62/832,944, filed Apr. 12, 2019, the entire disclosure of which is incorporated by reference herein.

BACKGROUND

Many electronic devices (e.g., smartphones, tablets, laptops, hearing aids, headphones, headsets, internet-of-things devices, etc.) include electronic microphones, for example microelectromechanical systems (MEMS) microphones. Such devices are often handled by users (e.g., carried, moved, picked up, put down, worn, etc.) and may therefore be susceptible to being dropped by a user. When dropped (or otherwise placed into freefall), the device accelerates downwards until the device contacts a sold surface (e.g., a floor). The resulting collision may cause damage to the device and/or the microphone. Accordingly, systems and methods for mitigating a risk of damage associated with such free fall events and/or tracking such events are desirable.

DETAILED DESCRIPTION

Figure 1:
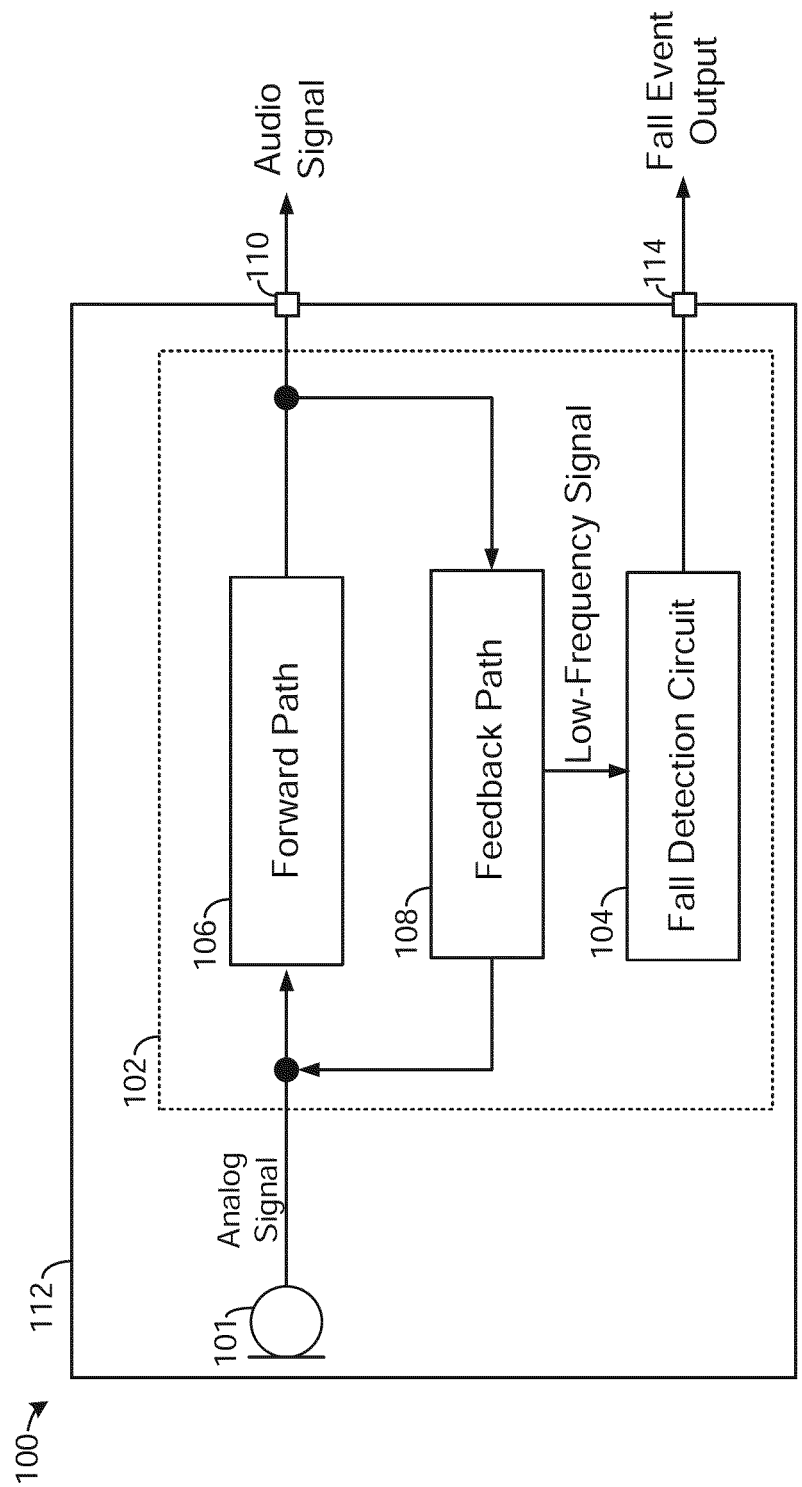
FIG. 1 is a first block diagram of a microphone assembly, according to an exemplary embodiment.

Referring generally to the FIGURES, one implementation of the present disclosure is a microphone assembly. The microphone assembly includes an acoustic transducer configured to generate an analog signal in response to pressure changes sensed by the acoustic transducer. The analog signal includes frequency components below a threshold frequency. The microphone assembly also includes an integrated circuit electrically coupled to the acoustic transducer and configured to determine a characteristic of frequency components below the threshold frequency, determine whether the characteristic of the frequency components corresponds to a fall event, and generate an output signal in response to a determination that the characteristic of the frequency components corresponds to the fall event. The microphone assembly also includes a housing having an external device interface with electrical contacts. The acoustic transducer and the integrated circuit are disposed within the housing. The integrated circuit is electrically coupled to contacts of the external device interface.

Another implementation of the present disclosure is an integrated circuit for use in a microphone assembly including a transducer disposed in a housing and configured to generate an electrical signal representative of changes in pressure sensed by the transducer. The integrated circuit is electrically connectable to the transducer and connectable to electrical contacts on a host interface of the microphone assembly. The integrated circuit includes a forward signal path including an analog-to-digital converter configured to convert an electrical signal received from the transducer to a digital signal when the integrated circuit is electrically coupled to the transducer, and processing circuitry coupled to the forward signal path and configured to determine a characteristic of frequency components of the digital signal. The frequency components are representative of change in ambient pressure. The processing circuitry is also configured to determine whether the characteristic of frequency components corresponds to a fall event and generate an output signal in response to a determination that the characteristic of frequency components corresponds to the fall event.

Another implementation of the present disclosure is a method in a microphone assembly including an electrical circuit electrically coupled to a transducer disposed in a housing. The method includes generating a signal in response to pressure changes sensed by the transducer. The signal includes frequency components below a threshold frequency representative of changes in ambient pressure and frequency components above the threshold frequency representative of voice activity. The method includes determining a characteristic of frequency components below the threshold frequency by electrically processing the signal, determining whether the characteristic of the frequency components corresponds to a fall event, and, in response to a determination that the characteristic of the frequency components corresponds to the fall event, configuring the microphone assembly to reduce a risk of damage associated with the fall event.

Referring now to FIG. 1, a block diagram of a microphone assembly 100 is shown, according to a first embodiment. As shown in FIG. 1, the microphone assembly 100 includes an acoustic transducer 101 and an integrated circuit 102 electrically coupled to the acoustic transducer 101. The acoustic transducer 101 and the integrated circuit 102 are disposed within a housing 112.

The acoustic transducer 101 is configured to sense pressure changes at the transducer 101, i.e., to generate an analog electrical signal indicative of changes in air pressure at the acoustic transducer 101. In some embodiments, the transducer can be implemented using microelectromechanical systems (MEMS) technology or using electret material. In other embodiments, the transducer is embodied as a MEMS piezoelectric or other transducer. In some embodiments, the transducer 101 can be a capacitive transducer.

The acoustic transducer 101 is configured to sense pressure changes in an acoustic/audible (e.g., human-perceptible) frequency range (i.e., sound) and lower-frequency pressure changes (e.g., lower than 30 Hz) in an ambient pressure frequency range, i.e., pressure changes which are indicative of an ambient pressure at the device. For example, in some embodiments the transducer 101 is configured to sense pressure changes with frequencies in a range of approximately 10 Hz to approximately 20 kHz. The acoustic transducer 101 outputs an analog signal including frequency components above a threshold frequency (which correspond to acoustic/audible pressure changes (i.e., sound)) and frequency components below the threshold frequency (which correspond to pressure changes associated with changes in ambient air pressure).

The low frequency components (e.g., below a threshold value of 30 Hz, below a threshold value of 20 Hz, below a threshold value of 10 Hz, etc.) are indicative of ambient pressure. Ambient pressure at the microphone assembly 100 is a function of elevation of the microphone assembly 100, i.e., a function of how much atmosphere is above the microphone. That is, ambient pressure decreases as elevation increases and vice versa. Accordingly, a change in ambient pressure at the microphone assembly 100 can correspond to a change in elevation of the microphone assembly 100, for example a change in a height of the microphone assembly 100 relative to a floor or other surface. Such a change in ambient pressure can result in a change in the low frequency pressure changes at the transducer 101. In such a case, the low frequency components of the analog signal generated by the transducer 101 are indicative of a change in elevation of the microphone assembly 100 and/or a rate of change in elevation of the microphone assembly 100.

The integrated circuit 102 is configured to receive the analog signal from the transducer 101 and process the analog signal to generate an electrical signal indicative of the audible/acoustic pressure changes at the transducer 101 (the "audio signal"). The integrated circuit 102 is also configured to determine a characteristic of the frequency components below the threshold frequency (i.e., the low frequency components), determine whether the characteristic of the frequency components corresponds to a fall event, and generate an output signal in response to a determination that the characteristic of the frequency components corresponds to the fall event. These and other features are described in detail below.

Figure 3:
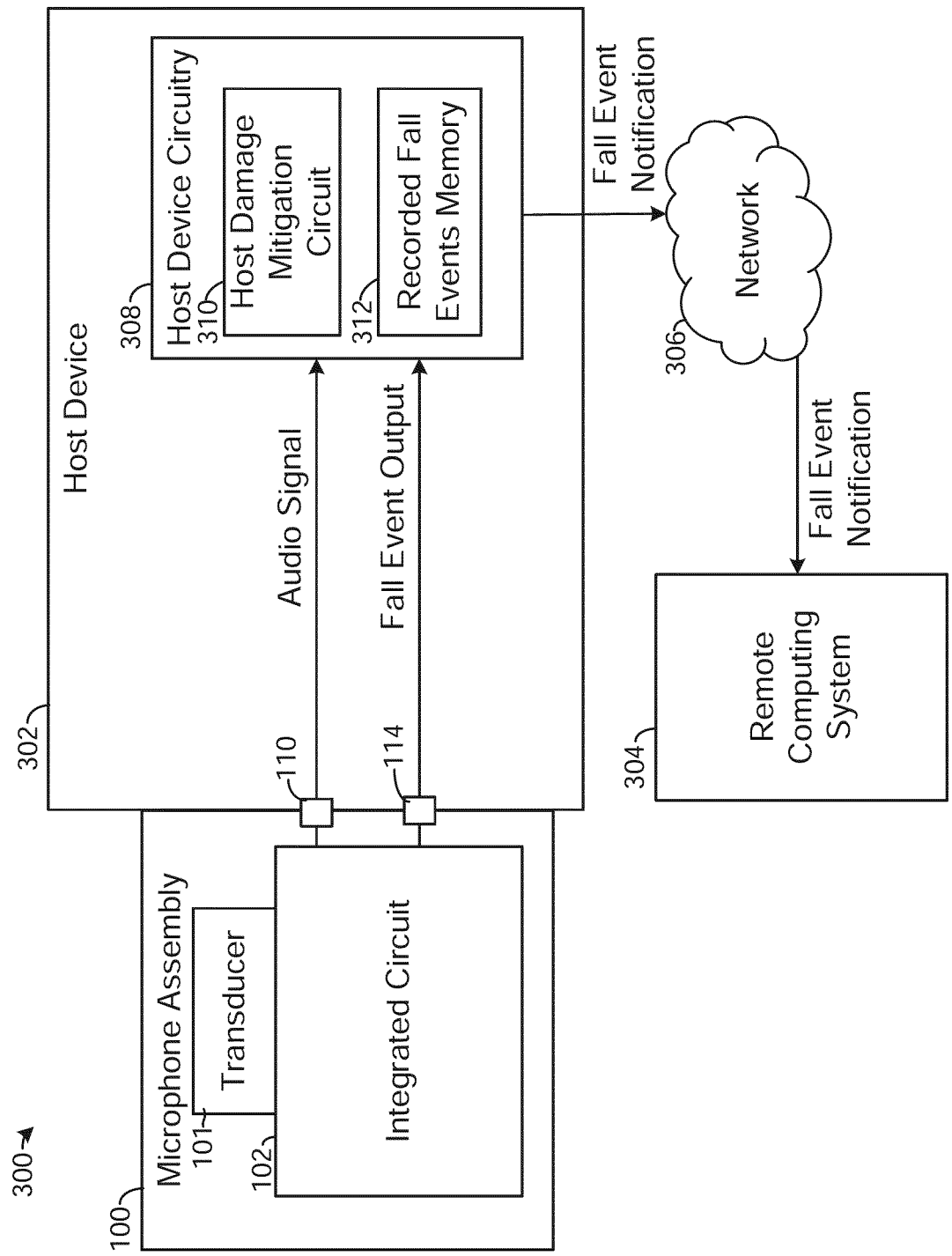
FIG. 3 is a block diagram of a computing system for use with the microphone assembly of FIGS. 1-2, according to an exemplary embodiment.

In FIG. 1, the integrated circuit 102 is shown to include a forward path 106, a feedback path 108, and a fall detection circuit 104. The forward path 106 amplifies the analog signal from the transducer 101 and may perform various analog-to-digital processing steps in various embodiments. For example, in some embodiments, the forward path 106 includes an amplifier and an analog-to-digital converter. The forward path 106 creates the audio signal (e.g., a digital signal) based on the analog signal received from the transducer 101. The audio signal is provided to a first electrical contact 110 located at a periphery of a housing 112 of the microphone assembly 100, where it can be communicated to an external electronic device (e.g., a host device as shown in FIG. 3).

The feedback path 108 is configured to receive the audio signal from the forward path 106, create a feedback signal based on the audio signal, and create a low-frequency signal that includes the low-frequency components of the signals. The feedback signal is provided to the forward path 106 and can be used to attenuate the low frequency components in the analog circuit to avoid saturation in amplification circuitry of the forward path 106. In some embodiments, the feedback path 108 includes a loop filter and a digital-to-analog converter. In such embodiments, the loop filter is configured to isolate low frequency components of the audio signal, while the digital-to-analog converter is configured to convert the filtered, digital signal to an analog signal that can be combined with the analog signal as shown in the feedback loop shown in FIG. 1.

As shown in FIG. 1, the feedback path 108 is configured to provide a low-frequency signal to the fall detection circuit 104. The low-frequency signal corresponds to the low-frequency pressure changes sensed by the transducer 101. For example, the feedback path 108 may include a low-pass filter configured to remove the high frequency components of the audio signal (or the analog signal) and pass through the low frequency components.

In the example of FIG. 1, the fall detection circuit 104 receives the low-frequency signal (e.g., digital low-frequency components of the audio signal) from the feedback path 108. In other embodiments, the fall detection circuit 104 receives the unprocessed analog signal from the transducer 101 or the full audio signal from the forward path 106. The fall detection circuit 104 is configured to determine a characteristic of the low frequency components, determine whether the characteristic corresponds to a fall event, and generate an output signal in response to a determination that the characteristic of the frequency components corresponds to the fall event.

For example, in some embodiments, the fall detection circuit 104 is configured to determine a present (current, real-time, etc.) frequency or period (i.e., the amount of time between oscillations) of the low frequency components, which corresponds to an ambient pressure at the present time. The fall detection circuit 104 can monitor the present frequency or period over time and track changes in the frequency or period which correspond to changes in ambient pressure, which, in turn, correspond to changes in elevation of the transducer 101.

In some embodiments, the fall detection circuit 104 is configured to calculate the rate of change of the frequency or period (i.e., a first derivative), which may correspond to the velocity of the transducer 101 in a vertical direction. In some embodiments, the fall detection circuit 104 is configured to calculate a rate of change of the rate of change of the frequency or period (i.e., a second derivative), which may correspond to the acceleration of the transducer 101 in the vertical direction. As used herein, the "characteristic" of the low frequency components can be any such frequency, period, change in period or frequency, a rate of such a change, a rate of change of said rate of change, etc.

The fall detection circuit 104 is configured to identify when the characteristic(s) of the low frequency components indicate that a fall event is occurring, i.e., that the microphone assembly 100 is in free fall or experiencing another type of fall event (e.g., a guided fall event as discussed below). For example, the fall detection circuit 104 may compare the second derivative of the frequency or period against a predetermined value associated with gravitational acceleration (i.e., at vertical acceleration of approximately $-9.8$ m/s$^2$). The predetermine value may be determined by laboratory testing. In this example, if the second derivative is within a tolerance of the predetermined value for at least a threshold amount of time, the fall detection circuit 104 determines that the microphone assembly 100 is in free fall. In some cases, the fall detection circuit 104 is configured to classify the fall event, for example based on a type of the fall (e.g., free fall or guided fall classified based on comparison to various predetermined fall event signatures) or based on a duration of the fall event. These and other examples of operations executable by the fall detection circuit 104 to detect and classify fall events are discussed below with reference to FIGS. 8-11.

In response to detecting a fall event, the fall detection circuit 104 generates an output signal (hereinafter the "fall event output"). In the example of FIG. 1, the fall event output is provided to a second electrical contact 114 positioned at a periphery of the housing. In such an embodiment, the fall event output is an electrical signal that includes an indication of the occurrence of the fall event. The fall event output may also include various other information relating to the fall event (e.g., a time of the fall event, a type of the fall event, a duration of the fall event). As shown in FIG. 1, the first electrical contact 110 and the second electrical contact 114 for an external device interface which is configured to be electrically coupled to an external device, for example to circuitry of a smartphone, tablet, hearing aid, headphone system, or other electronic device. The microphone assembly 100 of FIG. 1 is thus configured to provide the audio signal to the external device via the first electrical contact 110 and the fall event output to the external device via the second electrical contact 114. Subsequent operations executed by the external device and/or other computing systems are described below with reference to FIG. 3.

Figure 2:
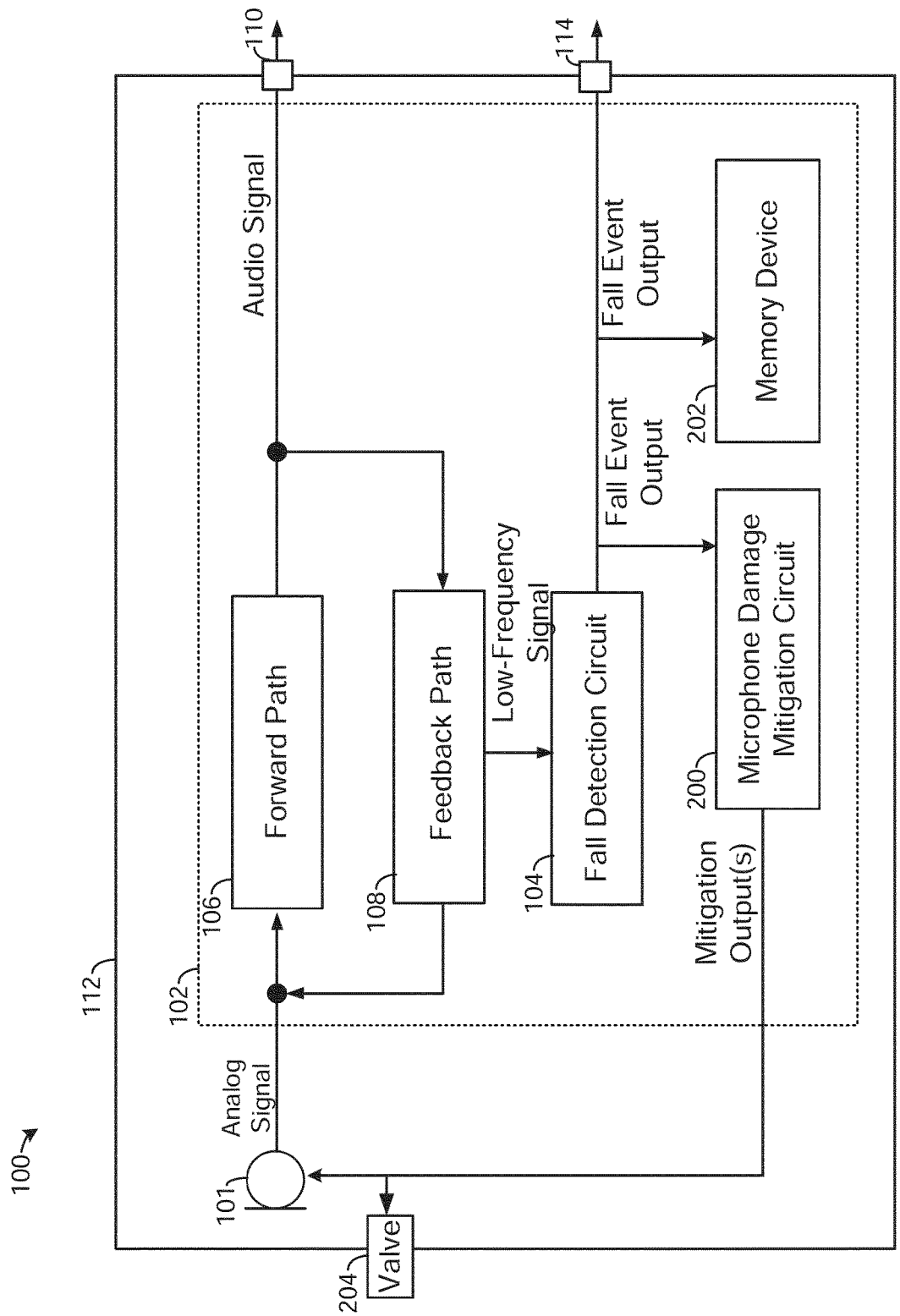
FIG. 2 is a second block diagram of a microphone assembly, according to an exemplary embodiment.

Referring now to FIG. 2, another embodiment of the microphone assembly 100 is shown. As shown in FIG. 2, the microphone assembly 100 includes the transducer 101, forward path 106, feedback path 108, fall detection circuit 104, housing 112, and electrical contacts 110, 114 as in FIG. 1. As shown in FIG. 2, the microphone assembly 100 also includes a microphone damage mitigation circuit 200, a memory device 202, and a valve 204. In the example shown, the microphone damage mitigation circuit 200 and the memory device 202 are included in the integrated circuit 102.

In some embodiments, the microphone assembly 100 includes a temperature sensor configured to measure a temperature at the microphone assembly and a compensation circuit included with the integrated circuit 102. In such configurations, the compensation circuit is configured to receive temperature measurements from the temperature sensor and modify the analog signal, the audio signal, and/or the low frequency signal to compensate for effects of temperature on operation of the transducer 101.

The memory device 202 is configured to receive the fall event output from the fall detection circuit 104 and store a record of the fall event. In response to receiving the fall event output, the memory device 202 is configured to store a data entry that indicates an occurrence of a fall event and, in some embodiments, indicates various other information about the fall event (e.g., a time of the fall event, a duration of the fall event, a type of the fall event). Over time, as multiple fall events occur, the memory device 202 may aggregate a history of the various fall events. The memory device 202 may be accessible to and/or provide the stored data entries to an external electronic device. For example, a user, service provider, vendor, maintenance technician, warranty or insurance provider, etc. may access the memory device 202 to determine whether a fall event has occurred. Such information may alter a value of the device, affect a warranty or insurance claim, or guide a plan for repair or maintenance of the device.

The microphone damage mitigation circuit 200 is configured to receive the fall event output from the fall detection circuit 104 and generate one or more mitigation outputs in response. A mitigation output causes a change in a configuration of the microphone assembly 100 in response to detection of the fall event that reduces a risk of damage associated with the fall event (i.e., associated with an impact with a floor or other surface that defines the end of a fall event).

For example, in some embodiments the microphone damage mitigation circuit generates a mitigation output that alters an operating point of the transducer 101 (e.g., a bias voltage across the transducer 101) in such a way that protects the transducer 101 from damage that might otherwise be suffered as a result of impact. As another example, the mitigation output may be configured to cause the transducer 101 to cease operation for a duration of the fall event.

Figure 6:
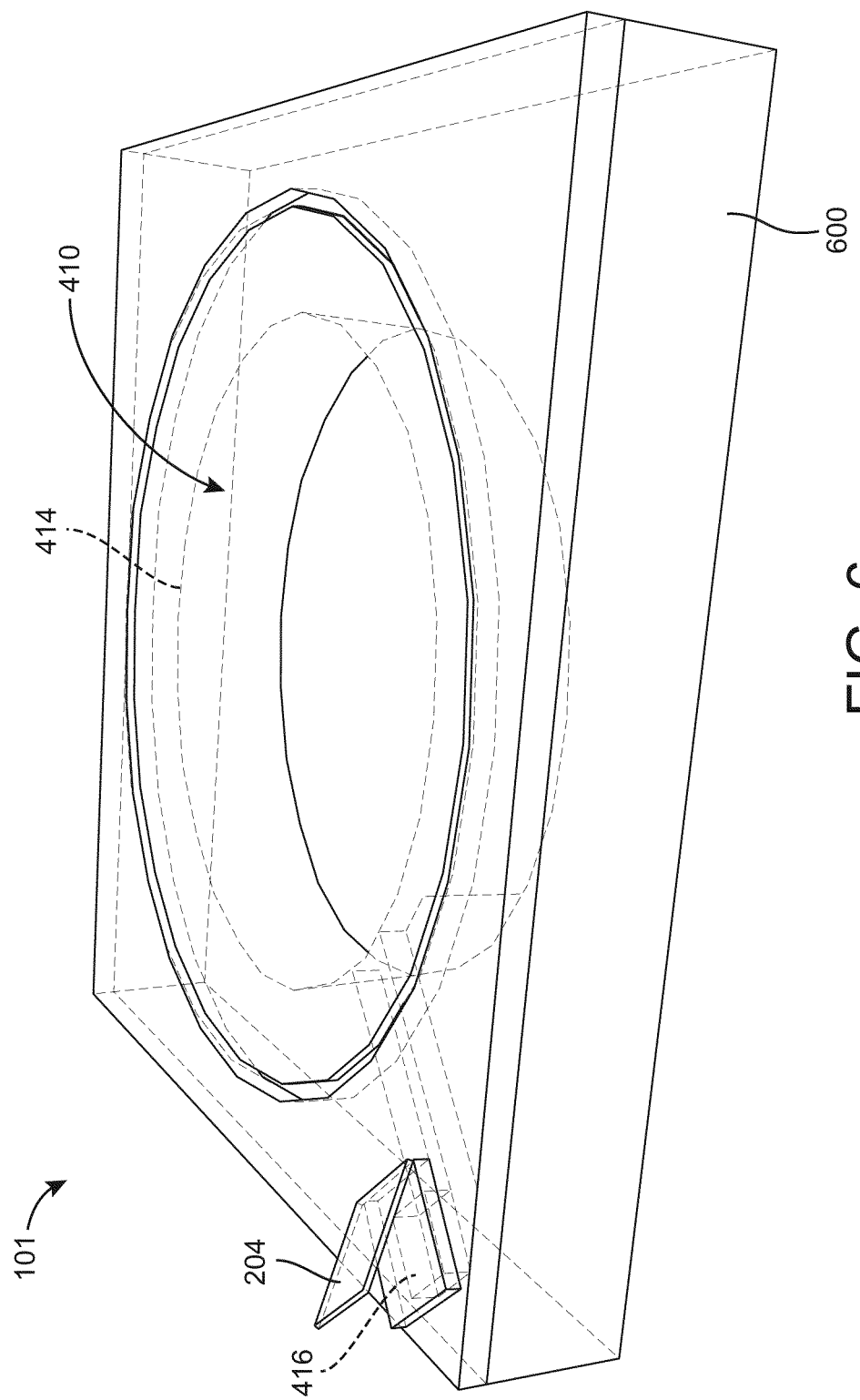
FIG. 6 is a perspective view of a portion of a microphone assembly, according to an exemplary embodiment.
Figure 7:
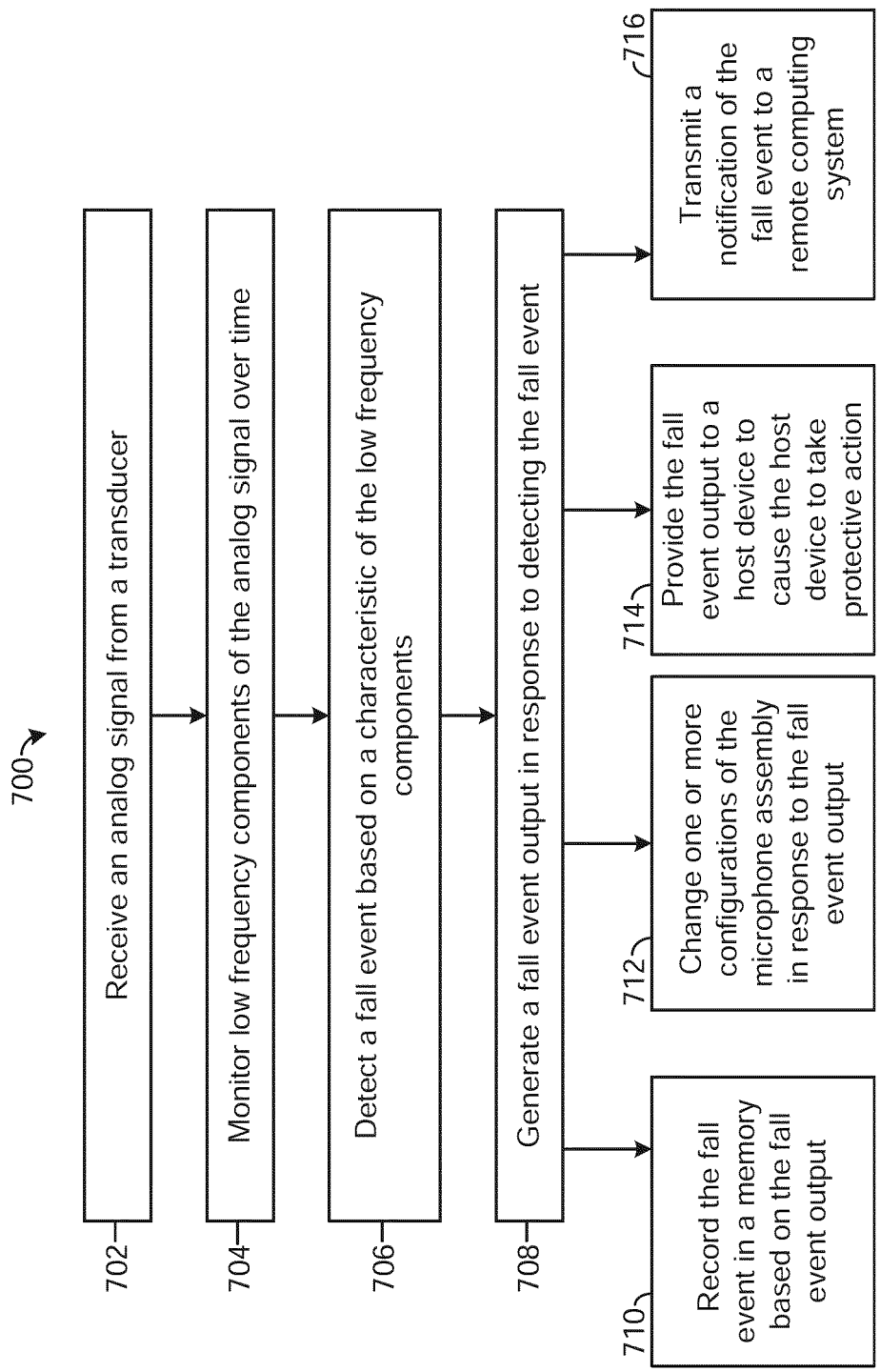
FIG. 7 is a flowchart of a process of detecting and responding to a fall event, according to an exemplary embodiment.

As another example, the microphone damage mitigation circuit 200 may generate a mitigation output that takes the form of a control signal for a valve 204 positioned on the housing 112 and electrically coupled to the integrated circuit 102. The valve 204 is configured to move to an open position to open an airway across the housing 112 (i.e., between an ambient environment and an interior of the housing 112) in response to the mitigation output. For example, in such a case, the mitigation output may include a voltage sufficient to cause actuation of the valve 204. The valve 204 may be configured to return to a closed position (in which the airway is substantially sealed) when the mitigation output is removed. Examples of the valve 204 are shown in FIGS. 6-7 and described in detail with reference thereto.

As shown in FIG. 2, the microphone assembly 100 is thereby configured to automatically detect that the microphone assembly 100 is experiencing a fall event and modify a configuration of the microphone assembly 100 to mitigate a risk of damage associated with the fall event. In some embodiments, the microphone assembly 100 is configured to perform such fall event detection and damage mitigation within the duration of the fall event, such that a protective action can be taken before impact of the microphone assembly 100 (or a device coupled to the microphone assembly 100) against a floor or other surface. Accordingly, the fall detection circuit 104 and the microphone damage mitigation circuit 200 are configured to execute the operations attributed thereto herein in less than an amount of time required for the microphone assembly 100 to fall a sufficient distance to cause damage to the microphone assembly 100, in some embodiments.

Referring now to FIG. 3, a system 300 for use with the microphone assembly 100 is shown, according to an exemplary embodiment. In the example shown, the microphone assembly is coupled to a host device 302, which is communicable with a remote computing system 304 via a network 306. In various embodiments, the host device 302 may be a smartphone, a tablet, a laptop computer, a smartwatch, a headset, other wearable technology, gaming console, hearing aid, etc. As shown in FIG. 1, the host device 302 (i.e., host device circuitry 308 of the host device 302) receives the audio signal from the integrated circuit 102 via the first electrical contact 110. The host device circuitry 308 may use the audio signal to provide various features to a user, for example to allow the user to make phone calls using the host device or to enter voice-based commands to the host device 302, among other possibilities.

The microphone assembly 100 is coupled to the host device 302 such that the pressure at the transducer 101 is the same as the pressure experienced at the host device 302, and such that the microphone assembly 100 moves with the same dynamics as the host device 302 (e.g., the same velocity, acceleration, etc.). Accordingly, when the microphone assembly 100 experiences a fall event as determined by the fall detection circuit 104 as described above, the host device 302 also experiences the fall event.

As shown in FIG. 3, the host device 302 receives the fall event output from the integrated circuit 102 via the second electrical contact 114. The host device 302 receives the fall event output at the host device circuitry 308, which is shown to include a host damage mitigation circuit 310 and a recorded fall events memory 312.

The host damage mitigation circuit 310 is configured to receive the fall event output and, in response to receiving the fall event output, modify a configuration of the host device 302 to reduce a risk of damage to the host device associated with the fall event. For example, the host damage mitigation circuit 310 may cause the host device 302 may increase or decrease power provided to various elements of the host device 302 to reduce a risk of damage to such elements. As another example, the host damage mitigation circuit may cause the host device 302 to turn off in response to the fall event signal. As another example, in some embodiments the host device may include a protective feature (e.g., airbag, etc.) that can be deployed on command from the host damage mitigation circuit 310 to dampen a collision between the host device and a surface (e.g., floor, ground) at the end of the fall event. Various damage mitigation functions are possible.

The recorded fall events memory 312 is configured to receive the fall event output and store a record (e.g., data entry) for the fall event. The recorded fall events memory 312 may store a time of the fall event, a duration/severity of the fall event, a type of the fall event, etc. for each fall event. The data stored by the fall events memory may be accessible to a user of the host device 302 via a user interface of the host device 302 (e.g., a display screen or touchscreen of the host device 302). The recorded fall events memory 312 may thereby facilitate a user in viewing a history of fall events associated with the host device 302.

FIG. 3 also illustrates that the host device 302 can be configured to transmit a fall event notification to a remote computing system 304 via a network 306. The network 306 may be a wireless network (e.g., WiFi, cellular network) or wired network (e.g., Ethernet). In some embodiments, the network 306 includes the Internet.

The remote computing system 304 is configured to receive the fall event notification and store a record of the fall event. The fall event notification may include information that identifies the host device 302, such that the remote computing system 304 can receive and organize fall event notifications from multiple host devices 302. The remote computing system 304 may be associated with a service provider relating to the host device 302, an insurer of the host device 302, a vendor of the host device 302, a maintenance/repair entity, etc. The remote computing system 304 may be accessible by such entities to monitor and investigate a history of fall events for the host device 302, for example to facilitate such an entity in addressing a warranty or insurance claim by a user of the host device 302.

As another example, the remote computing system 304 may be associated with a health care provider or emergency response system. In such an example, the host device 302 may be a hearing aid or other wearable device, and a fall event detected by the microphone assembly 100 may be indicative a fall also suffered by the person wearing the host device 302. For example, the fall detection circuit 104 may be configured to classify a fall event as an emergency or human-carried fall event (i.e., in which the microphone assembly 100 falls while still connected to a person) based on dynamics of the fall and characteristics of the low frequency components of the signal generated by the transducer 101. In such an example, the remote computing system 304 may be configured to automatically generate a warning/alarm, contact emergency assistance (e.g., paramedics, emergency responders, healthcare staff, family members), or otherwise facilitate the provision of physical assistance for the user.

It should be appreciated that, while FIG. 2 illustrates an implementation in which the microphone assembly can perform damage mitigation and recordation in relation to detected fall events and FIG. 3 illustrates an implementation in which the host device performs such features, in other implementations, some such features can be implemented in the microphone assembly and others can be implemented in the host device. For example, in some embodiments, the microphone assembly may include features for recording fall events to memory but not mitigation features, or vice versa, and the host device may include features for mitigating the fall events but not recording the fall events to memory, or vice versa. In other implementations, both the microphone assembly and the host device may include both recording and mitigation features, and, in some such implementations, different types of features (e.g., different types of mitigation features) may be implemented in the microphone assembly and the host device (e.g., the microphone assembly may take actions to prevent damage to the microphone assembly while the host device may take actions to prevent damage to the host assembly and/or report the fall event to other systems/parties). All such various implementations are contemplated within the scope of the present disclosure.

Figure 4:
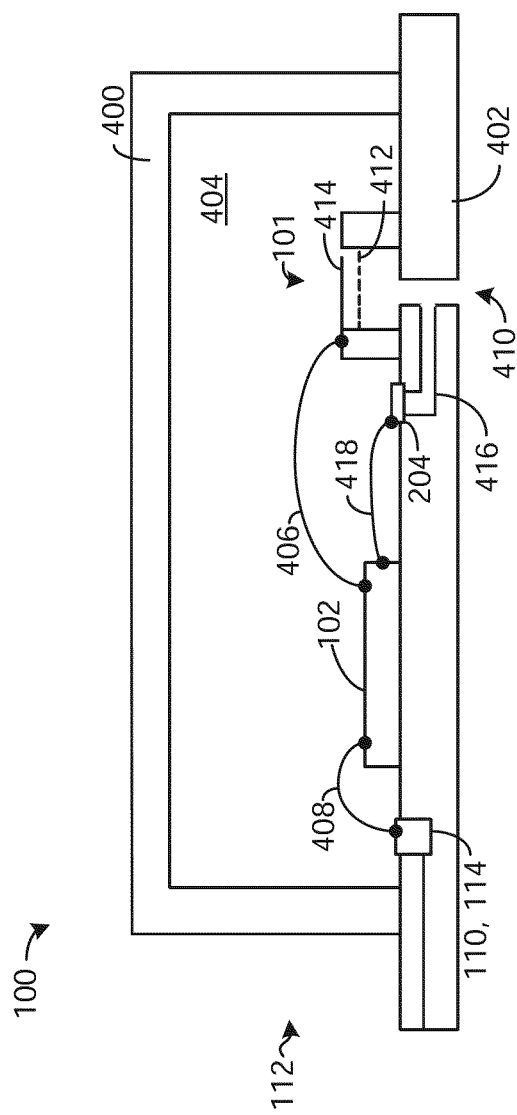
FIG. 4 is a cross-sectional view of a microphone assembly, according to an exemplary embodiment.

Referring now to FIG. 4, a cross-sectional view of a microphone assembly 100 is shown, according to an exemplary embodiment. The cross-sectional view of FIG. 4 shows the transducer 101 and the integrated circuit 102 disposed within the housing 112. The housing 112 is shown to include a board 402 and a lid 400. The lid 400 is positioned over the board 402 to define an interior volume 404 between the board 402 and the lid 400. The transducer 101 and the integrated circuit 102 are positioned in the interior volume 404. The transducer 101 is shown as electrically coupled to the integrated circuit 102 by a first conductive pathway 406. The integrated circuit 102 is shown as electrically coupled to the first and second electrical contacts 110, 114 of the external device interface by a second conductive pathway 408.

The transducer 101 is positioned over a sound port 410 that extends through the board 402. The transducer 101 includes a diaphragm 412 and a backplate 414. The sound port 410 allows communication of pressure (i.e., airflow) from the exterior of the housing 112 (i.e., from an ambient environment) to the diaphragm 412.

As shown in FIG. 4, an airway 416 extends from the sound port 410 to the interior volume 404 of the housing 112. The airway 416 provides a bypass around the transducer 101 that allows airflow from the ambient environment to the interior volume 404 of the housing 112 without requiring the airflow to pass by or through the transducer 101.

A valve 204 is positioned at the airway 416. The valve 204 is controllable by the integrated circuit 102 (e.g., by the microphone damage mitigation circuit 200) between a closed position and an open position. In the closed position, the valve 204 substantially prevents airflow through the airway 416 between the ambient environment and the interior of the housing 112, such that any pressure differentials are pneumatically communicated to and experienced by the transducer 101. In the open position, the valve 204 allows airflow through the airway 416 between the ambient environment and the interior of the housing 112, which may result in a decreased pressure differential across the transducer 101. Thus, by controlling the valve 204 to the open position, a risk of damage to the transducer 101 caused by excessive pressure differentials (e.g., which may be associated with a collision at the end of a fall event) is reduced.

The valve 204 is electrically coupled to the integrated circuit 102 by a third conductive pathway 418 that allows the integrated circuit 102 to provide control signals (e.g., voltages) to the valve 204. For example, the valve 204 may be biased to the closed position, such that the valve 204 remains in the closed position unless a sufficient voltage is received from the integrated circuit 102. Example configurations of the valve 204 are shown in FIGS. 5-6.

Figure 5:
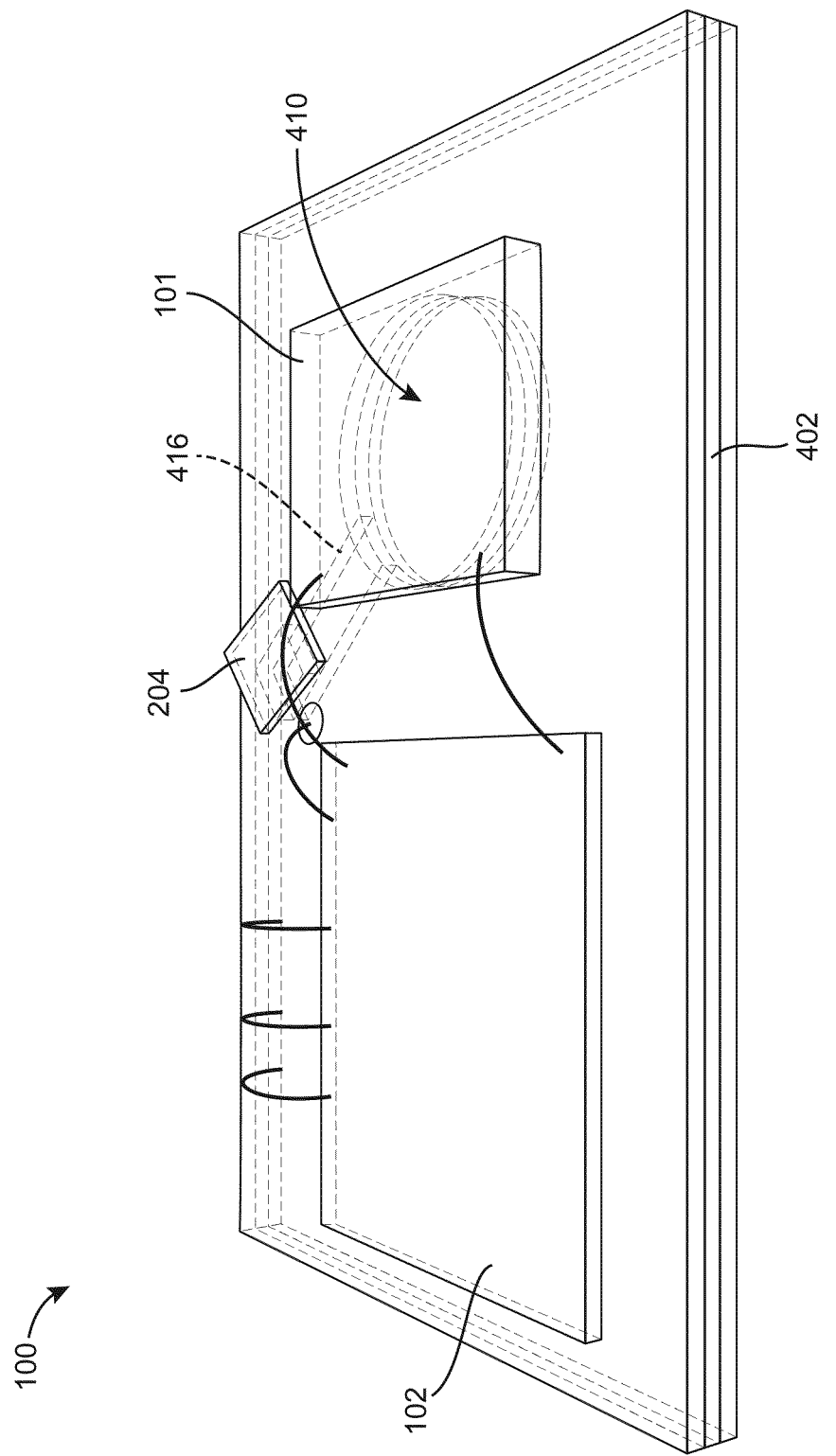
FIG. 5 is a perspective view of a portion of a microphone assembly, according to an exemplary embodiment.

Referring now to FIG. 5, a perspective view of an embodiment of the microphone assembly 100 is shown, according to an exemplary embodiment. FIG. 5 shows the microphone assembly 100 without the lid 400 to better show other components of the microphone assembly 100. As shown in FIG. 5, the transducer 101 is positioned over the sound port 410 which extends through the board 402. The airway 416 extends through the board 402 form the sound port 410 to a position on the board 402 separated from the transducer 101. The valve 204 is shown positioned over the airway 416 on the board 402. The valve 204 is shown as a flap that can be electrically controlled to rotated away from the airway 416 to open the airway 416 (i.e., to move to the open position shown in FIG. 5 to allow airflow through the airway 416. In other embodiments, the valve 204 may be any of various types of valves.

Referring now to FIG. 6, a perspective view of the transducer 101 is shown, according to an exemplary embodiment. In the example shown, the transducer 101 includes a can 600 configured to extend upward from the board 402 to support the diaphragm 412 and backplate 414. In the example of FIG. 6, the airway 416 extends from an interior of the can 600 to an exterior of the can 600 to bypass the diaphragm 412 and backplate 414. The valve 204 is shown in an open position. As shown, the valve 204 includes a flap that can be electrically controlled to rotate away from the airway 416 to open the airway 416. In other embodiments, the valve 204 may be any of various types of valves.

Referring now to FIG. 7, a flowchart of a process 700 for detecting and responding to a fall event is shown, according to an exemplary embodiment. The process 700 can be executed by the integrated circuit 102 of the microphone assembly 100.

At step 702, an analog signal is received from the transducer 101. As described in detail above, the analog signal can include high frequency components corresponding to acoustic/audible pressure changes (e.g., human-perceptible sound) and low frequency components corresponding to the ambient air pressure at the transducer 101.

At step 704, the low frequency components of the analog signal are monitored over time. For example, a characteristic of the low frequency components may be determined for a current time step and updated as time progresses. For example, the integrated circuit 102 may determine a frequency or period of the low frequency components for a current time step. The integrated circuit 102 may also determine a first or second derivative of the frequency or period for a current time step. In such a case, the integrated circuit 102 may collect a dataset by determining the frequency or period for a series of adjacent time steps and determine the first or second derivative based on the dataset.

In various embodiments, the integrated circuit 102 may monitor various characteristics, metrics, etc. relating to the low frequency components of the analog signal from the transducer 101.

Figure 8:
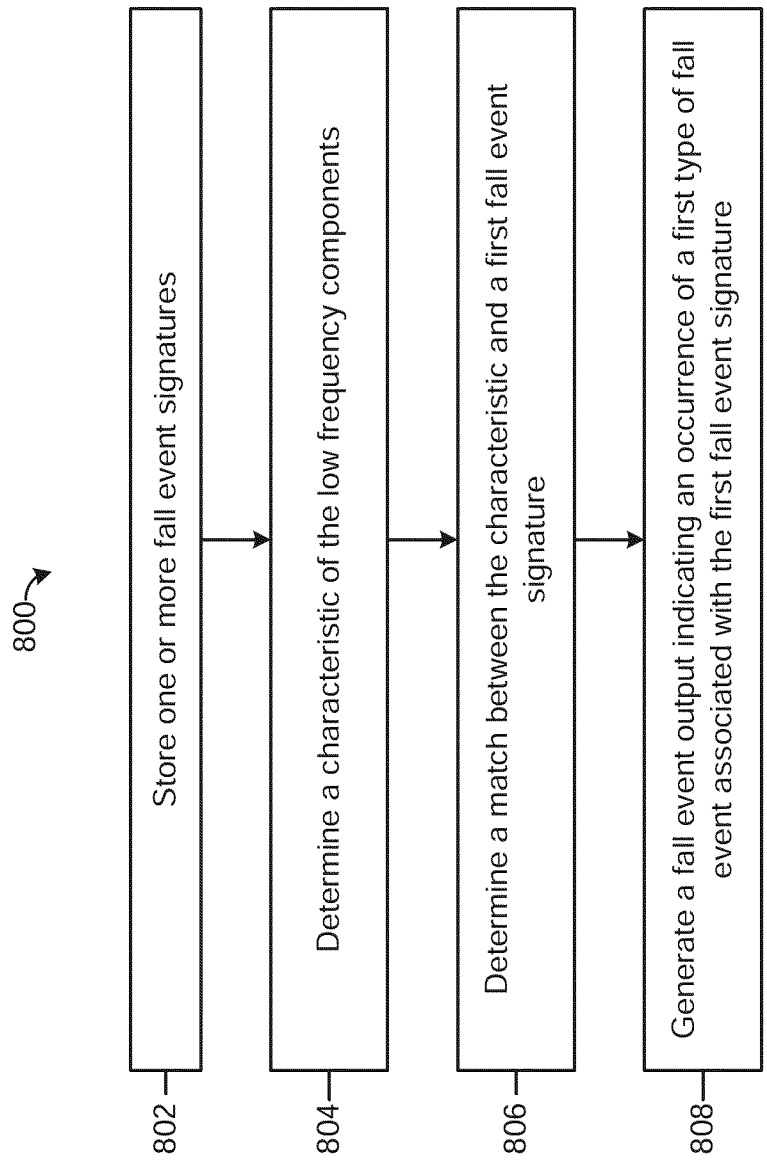
FIG. 8 is a flowchart of a process for detecting and categorizing a fall event, according to an exemplary embodiment.

At step 706, a fall event is detected based on a characteristic of the low frequency components. An example process for detecting a fall event based on a characteristic of the low frequency components is shown in FIG. 8 and described with reference thereto below. In some cases, the fall event is detected in real-time during the fall event, i.e., while the microphone assembly 100 is falling and before the microphone assembly 100 collides with a floor or other surface to end the fall event.

At step 708, a fall event output is generated in response to detecting the fall event. The fall event output may be generated by the integrated circuit 102 during the fall event. The fall event output may be an analog or digital electrical signal that includes information relating to the fall event (e.g., indicating occurrence of the fall event).

In various embodiments, the fall event output may initiate one or more of various responses to the fall event as shown in steps 710-716. Each of steps 710-716 is optional, such that in a given implementation or in response to a given fall event output one or more of the steps 710-716 may be executed. In various embodiments, one or more of steps 710-716 occur during the fall event, i.e., before impact of the microphone assembly 100 and/or host device 302 with a floor or other surface.

At step 710, the fall event is recorded in a memory based on the fall event signal. For example, as described with reference to FIG. 2, the fall event output may be provided to a memory device 202 of the integrated circuit 102 and a record of the fall event can be created and stored by the memory device 202. As another example, as described with reference to FIG. 3, the fall event output may be provided to a host device 302 and stored in a recorded fall events memory 312 of the host device 302.

At step 712, one or more configurations of the microphone assembly 100 are changed in response to the fall event signal. The microphone assembly 100 may be transitioned from an operational configuration (in which the microphone assembly 100 can provide an accurate audio signal indicative of the acoustic activity proximate the microphone assembly 100) to a protective configuration (in which the microphone assembly 100 is adapted to reduce a risk of damage associated with the fall event). For example, in the example of FIG. 2, the microphone damage mitigation circuit 200 can generate a control signal that causes the valve 204 to open in response to fall event signal. As another example, the microphone damage mitigation circuit 200 can modify the voltage differential across the transducer 101 to reduce a risk of damage to the transducer 101. Various protective configurations are possible.

At step 714, the fall event output is provided to a host device 302 to cause the host device 302 to take protective action. In such embodiments, the integrated circuit 102 may push the fall event output to the host device 302 via the second electrical contact 114. The fall event output generated by the integrated circuit 102 may be configured to cause the host device 302 to automatically apply a protective action, for example by modifying one or more configurations of the host device 302 in response to the fall event output. Various protective steps are possible depending on the features and capabilities of the host device 302. The microphone assembly 100 may be configured to be compatible with various types of host devices 300 (e.g., devices 300 with various manufacturers, models, features, functions, etc.).

At step 716, a notification of the fall event is transmitted to a remote computing system. For example, as shown in FIG. 3, the fall event output may be configured to cause the host device 302 to generate a fall event notification and transmit the fall event notification to the remote computing system 304 via a network 306 (e.g., via the Internet). The remote computing system 304 receives, stores, and/or otherwise processes the fall event notification.

Figure 9:
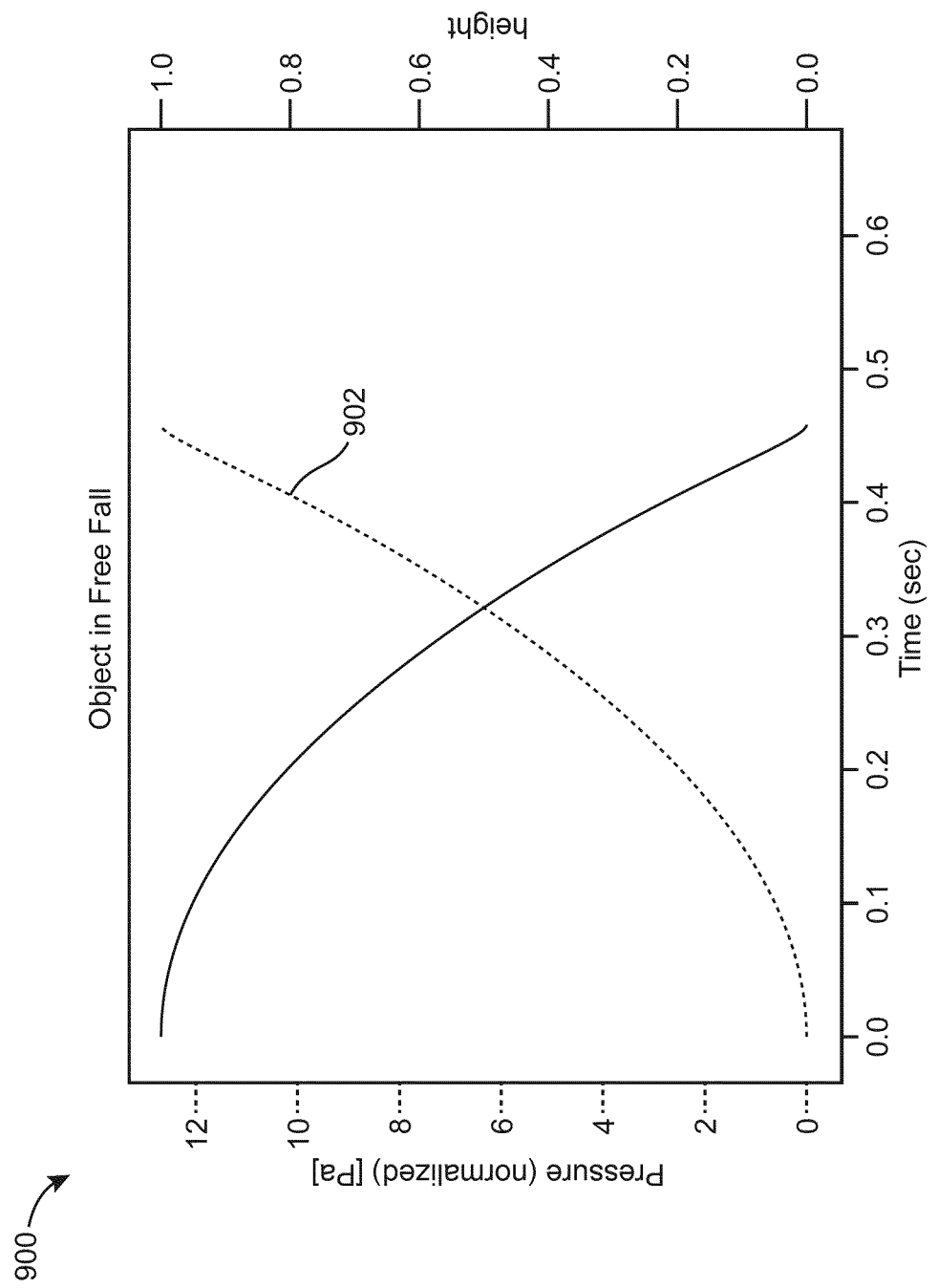
FIG. 9 is a graph of a pressure and height data corresponding to a free fall event, according to an example experiment.
Figure 10:
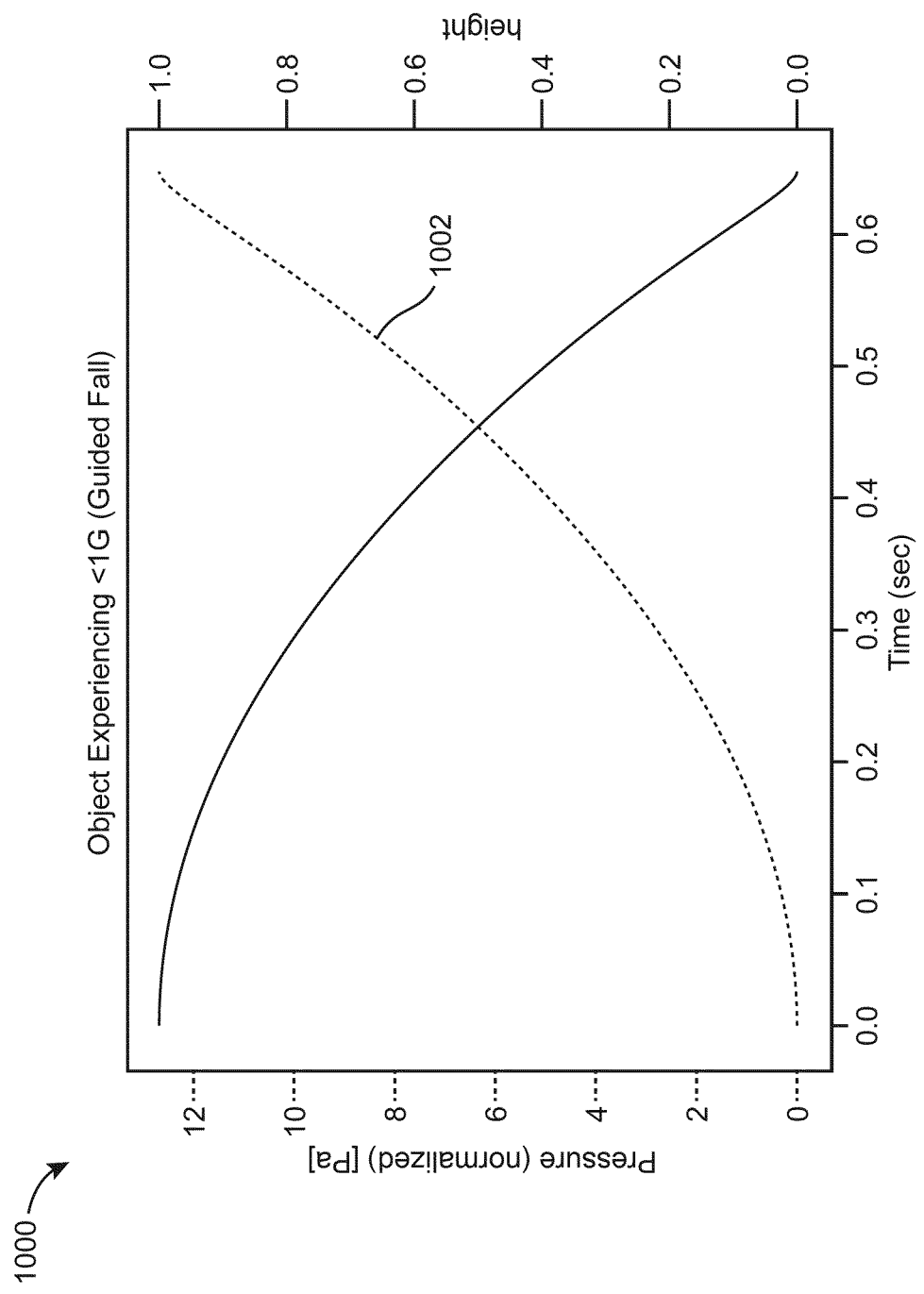
FIG. 10 is graph of pressure and height data corresponding to a guided fall event, according to an example experiment.

Referring now to FIG. 8, a flowchart of a process 800 for detecting a fall event based on a characteristic of the low frequency components of the analog signal created by the transducer 101 is shown, according to an exemplary embodiment. FIGS. 9-10 show example graphs of pressure and height curves useful for illustrating the steps of process 800, and reference is made thereto in the following description of FIG. 8. In some embodiments, process 800 can be executed by the integrated circuit 102. In some embodiments, one or more steps of process 800 are executed by the host device 302 and/or the remote computing system 304. Process 800 includes a possible implementation of steps 704-708 of process 700.

At step 802, the one or more fall event signatures are stored. Each of the fall event signatures corresponds to a type of fall event. A fall event signature is one or more of a value, curve, trajectory, trait, etc. of the characteristic of the low-frequency components of the analog signal from the transducer 101 which is associated with a fall event of a particular type.

For example, FIG. 9 shows a graph 900 of pressure and height over time for an object (e.g., a microphone assembly 100) in free fall. Because of the substantial uniformity of the force of gravity and given a negligible amount of air resistance, the graph 900 of pressure and height over time is substantially accurate at any location on Earth and for substantially any microphone assembly 100 or host device 302. A fall event signature can be defined based on the graph 900. For example, the fall event signature for a freefall-type event may be a function that describes the pressure curve 902 shown on the graph 900. As another example, the fall event signature can be a value of a second derivative of the function that describes the pressure curve 902, i.e., an "acceleration" of the pressure which, as shown by graph 900, maps to an acceleration of a position of an object in the height dimension (i.e., parallel to gravity). From physical principles, the second derivative of the pressure curve may be a scalar multiple of the substantially-constant gravitational acceleration near the surface of the Earth (i.e., a multiple of approximately 9.8 m/s/s). Thus, a fall event signature for a freefall-type event can be the value of the second derivative of the pressure curve 902. Because the pressure values that make up the pressure curve 902 can be linearly related to the frequency or period of the low frequency components generated by the transducer 101, the fall event signature may be defined as a particular value of the second derivative of the frequency or period of the low frequency components or other corresponding pattern of the frequency or period.

As another example, FIG. 10 shows a graph 1000 of pressure and height over time for an object (e.g., a microphone assembly 100) experiencing a guided fall at less than gravitational acceleration. For example, the guided fall may correspond to a user setting down a host device 302 that includes the microphone assembly 100 in a controlled manner. As another example, the guided fall may correspond to a user collapsing/falling/tripping/etc. while holding or wearing the host device 302. As illustrated by FIG. 10, the pressure curve 1002 of the graph 1000 has a different shape than the pressure curve 902 of FIG. 9 for the freefall-type event. In particular, the value of the second derivative of the pressure curve 1002 is lower (in absolute value) than the value of the second derivative of the pressure curve 902 of FIG. 9. Accordingly, a fall event signature for a guided fall event can be defined based on the value of the second derivative of the pressure curve 1002.

Accordingly, multiple fall event signatures corresponding to different types of fall events can be stored at step 802, for example in a memory device of the fall detection circuit 104.

At step 804, a characteristic of the low frequency components is determined. The characteristic determined at step 804 is a type of information that matches the criteria defined by the fall event signature. For example, if the one or more fall event signatures are defined as second derivatives of pressure, at step 804 a present value of the second derivative of the pressure is determined based on the low frequency components.

At step 806, a match between the characteristic and a first fall event signature is determined. For example, if the characteristic determined at step 804 is a numerical value (e.g., of a second derivative of pressure) and the first fall event signature is a numerical value, at step 806 the integrated circuit 102 may determine whether the characteristic is approximately equal to the first fall event signature (e.g., different from the first fall event signature by less than a threshold amount). In some cases, a match between the characteristic and the first fall event signature may require substantially equivalency between the current value for the characteristic and the first fall event signature for at least a threshold duration.

At step 808, a fall event output is generated that indicates an occurrence of a first type of fall event associated with the first fall event signature. In the example of FIG. 8, the fall event output includes an indication of the type of the fall event, e.g., which of multiple fall event signatures matched the characteristic of the low frequency components. Step 808 corresponds to step 708 of FIG. 7. Accordingly, process 700 may proceed at steps 710-716 following step 808. In some cases, the type of fall event indicated by the fall event output determines which of steps 710-716 are executed.

The foregoing description of illustrative embodiments has been presented for purposes of illustration and of description. It is not intended to be exhaustive or limiting with respect to the precise form disclosed, and modifications and variations are possible in light of the above teachings or may be acquired from practice of the disclosed embodiments. It is intended that the scope of the invention be defined by the claims appended hereto and their equivalents.

What is claimed is:

1. A microphone assembly comprising:
   an acoustic transducer configured to generate an analog signal in response to pressure changes sensed by the acoustic transducer, the analog signal comprising frequency components below a threshold frequency;
   an integrated circuit electrically coupled to the acoustic transducer and configured to:
   determine a characteristic of frequency components below the threshold frequency;
   determine whether the characteristic of the frequency components corresponds to a fall event; and
   generate an output signal in response to a determination that the characteristic of the frequency components corresponds to the fall event; and a housing having an external device interface with electrical contacts, the acoustic transducer and the integrated circuit disposed within the housing, the integrated circuit electrically coupled to contacts of the external device interface.

2. The assembly of claim 1, wherein the integrated circuit is configured to temporarily change a configuration of the microphone assembly in response to the output signal, and wherein the change in the configuration reduces a risk of damage to the microphone assembly due to the fall event.

3. The assembly of claim 2, wherein the configuration comprises a bias voltage applied to the acoustic transducer.

4. The assembly of claim 1, wherein the integrated circuit is configured to store an indication of the fall event in a memory device.

5. The assembly of claim 1, wherein the acoustic transducer is configured to generate the analog signal in response to detecting voice activity and changes in ambient pressure, the voice activity predominately represented by frequency components above the threshold frequency and the changes in ambient pressure predominately represented by frequency components below the threshold frequency.

6. The assembly of claim 1, wherein the housing comprises:
a sound port over which the acoustic transducer is disposed;
an airway extending from the sound port to an interior of the housing; and
a valve positioned at the airway and controllable to open the airway in response to the output, wherein the open airway circumvents the acoustic transducer.

7. The assembly of claim 1, wherein the characteristic comprises a second derivative of ambient pressure represented by frequency components below the threshold frequency.

8. The assembly of claim 1, wherein the integrated circuit is configured to determine whether the characteristic of the frequency components corresponds to the fall event based on a comparison of the characteristic of the frequency components to a fall event signature.

9. An integrated circuit for use in a microphone assembly including a transducer disposed in a housing and configured to generate an electrical signal representative of changes in pressure sensed by the transducer, the integrated circuit electrically connectable to the transducer and connectable to electrical contacts on a host interface of the microphone assembly, integrated circuit comprising:
a forward signal path including an analog-to-digital converter (ADC) configured to convert an electrical signal received from the transducer to a digital signal when the integrated circuit is electrically coupled to the transducer; and
processing circuitry coupled to the forward signal path and configured to:
determine a characteristic of frequency components of the digital signal, the frequency components representative of change in ambient pressure;
determine whether the characteristic of frequency components corresponds to a fall event; and
generate an output signal in response to a determination that the characteristic of frequency components corresponds to the fall event.

10. The circuit of claim 9 further comprising a lowpass digital filter coupled to the forward signal path and configured to filter the digital signal, the processing circuit coupled to the forward signal path by the lowpass digital filter and configured to determine whether the characteristic of frequency components corresponds to the fall event after the digital signal is filtered by the lowpass digital filter.

11. The circuit of claim 9, wherein the processing circuitry is further configured to cause a memory device to store a record of the fall event.

12. The circuit of claim 9, wherein the output signal is a transducer bias voltage signal having a polarity and magnitude configured to reduce risk of damage to the transducer by the fall event when the transducer is electrically coupled to the integrated circuit.

13. The integrated circuit of claim 9, wherein the output signal is a valve actuation control signal.

14. The integrated circuit of claim 9, wherein the characteristic comprises a second derivative of an ambient pressure represented by the frequency components of the digital signal.

15. The integrated circuit of claim 9, wherein the processing circuitry is configured to determine whether the characteristic of the frequency components corresponds to the fall event based on a comparison of the characteristic of the frequency components to a fall event signature.

16. A method in a microphone assembly including an electrical circuit electrically coupled to a transducer disposed in a housing, the method comprising:
generating a signal in response to pressure changes sensed by the transducer, the signal comprising frequency components below a threshold frequency representative of changes in ambient pressure and frequency components above the threshold frequency representative of voice activity;
determining a characteristic of frequency components below the threshold frequency by electrically processing the signal;
determining whether the characteristic of the frequency components corresponds to a fall event;
in response to a determination that the characteristic of the frequency components corresponds to the fall event, configuring the microphone assembly to reduce a risk of damage associated with the fall event.

17. The method of claim 16, wherein the characteristic of frequency components comprises a second derivative of ambient pressure.

18. The method of claim 16, wherein determining whether the characteristic of the frequency components corresponds to a fall event comprises comparing the characteristic of the frequency components to a fall event signature.

19. The method of claim 16, wherein configuring the microphone assembly to reduce a risk of damage associated with the fall event comprises opening a valve of the microphone assembly.

20. The method of claim 16, comprising storing a record of the fall event in a memory device.

* * * * *